United States Patent [19]

Schell et al.

[11] 3,956,408

[45] May 11, 1976

[54] PREPARATION OF UNSATURATED ALCOHOLS

[75] Inventors: Raymond A. Schell, Oxford; Lawrence J. Kehoe, Huntington Woods, both of Mich.

[73] Assignee: Ethyl Corporation, Richmond, Va.

[22] Filed: June 5, 1975

[21] Appl. No.: 583,880

Related U.S. Application Data

[63] Continuation-in-part of Ser. No. 322,470, Jan. 10, 1973, abandoned, which is a continuation-in-part of Ser. No. 49,160, June 23, 1970, abandoned, which is a continuation-in-part of Ser. No. 776,788, Nov. 18, 1968, abandoned.

[52] U.S. Cl. ..................... 260/638 R; 260/614 AA; 260/617 R; 260/618 R; 260/618 D; 260/633; 260/635 R; 260/681; 260/682; 260/642 R
[51] Int. Cl.$^2$ ................... C07C 29/00; C07C 27/00
[58] Field of Search ........ 260/638 R, 617 R, 618 R

[56] References Cited

UNITED STATES PATENTS

| | | | |
|---|---|---|---|
| 3,574,773 | 4/1971 | Mueller et al. | 260/638 R |
| 3,674,889 | 7/1972 | Schell et al. | 260/638 R |
| 3,798,278 | 3/1974 | Jung | 260/618 R |

*Primary Examiner*—Joseph E. Evans
*Attorney, Agent, or Firm*—Donald L. Johnson; Robert A. Linn

[57] ABSTRACT

A process for preparing unsaturated organic compounds by reacting an allylic alcohol and a ketone or aldehyde, in the presence of carbon monoxide and a Group VIII metal salt/germanium or tin salt combination catalyst is described. The unsaturated organic compounds are principally unsaturated alcohols having a molecular weight greater than the allylic alcohol reactant.

18 Claims, No Drawings

PREPARATION OF UNSATURATED ALCOHOLS

CROSS REFERENCE TO RELATED APPLICATIONS

This application is a continuation-in-part of copending application Ser. No. 322,470, filed Jan. 10, 1973, now abandoned which in turn is a continuation-in-part of Ser. No. 49,160, filed June 23, 1970, now abandoned, which in turn is a continuation-in-part of Ser. No. 776,788, filed Nov. 18, 1968, now abandoned.

BACKGROUND OF THE INVENTION

The present invention is directed to a novel catalytic reaction of an allylic alcohol and a ketone or aldehyde in the presence of carbon monoxide and a catalyst.

The reaction of olefins with carbon monoxide and an alkanol in the presence of a Group VIII metal salt/tin or germanium salt combination catalyst is known to produce carboxylic acid esters (see U.S. Pat. No. 2,876,254). This catalyst system is also known to isomerize double bonds of olefins; for example, hexene-1 is converted to hexene-2 and hexene-3.

It has been discovered that surprisingly an allylic alcohol and a ketone or aldehyde will react in the presence of carbon monoxide, and a Group VIII metal salt/germanium or tin salt combination catalyst to produce unsaturated organic compounds having a molecular weight substantially greater than the allylic alcohol; these unsaturated organic compounds are principally unsaturated alcohols.

SUMMARY OF THE INVENTION

A process for the preparation of mono-unsaturated alcohols from the reaction of an allylic alcohol and a carbonyl compound selected from ketones and aldehydes in the presence of carbon monoxide, a catalytic amount of a Group VIII metal salt/tin, or germanium salt catalyst combination.

DESCRIPTION OF THE PREFERRED EMBODIMENTS

An embodiment of this invention is a process for preparing mono-olefinically unsaturated alcohols from the reaction of an allylic alcohol having the formula

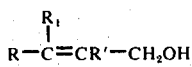

wherein R, R' and $R_1$ are independently selected from the group consisting of hydrogen and hydrocarbon alkyl, cycloalkyl, aryl, and aralkyl groups having from one to about 27 carbon atoms, and carbonyl compound in the presence of carbon monoxide, and a catalytic amount of a catalyst combination of (a) a salt of a Group VIII noble metal and (b) a salt of a metal selected from tin and germanium. A preferred embodiment of this invention is a process in which R' in the allylic alcohol illustrated above is hydrogen, and in a more preferred embodiment, R' and R or $R_1$ are hydrogen. $C_3$–$C_{10}$ alkyl ketones and $C_1$–$C_{10}$ alkyl aldehydes are preferred carbonyl compounds. A catalyst combination featuring salts of platinum is more preferred; combinations of platinum containing halides and tin halides are especially preferred. The process of the present invention will be described in more detail below.

Allylic alcohols which are useful in the practice of the present invention are those having the following formula

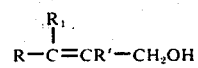

I

R, R' and $R_1$ in Formula I can be hydrogen and/or monovalent organic radicals. When R, R' and $R_1$ are monovalent organic radicals, these radicals should be such that they do not adversely affect the reaction in the present process. The hydrocarbon radicals which are represented by R, R' and $R_1$ include aryl groups, alkyl groups, alkaryl groups and aralkyl groups, having from one to about 27 carbon atoms, such that the total number of carbon atoms in the allylic alcohol does not exceed about 30. Examples of suitable organic radical substituents are aryl groups, such as phenyl, alkylated phenyls, such as tert-butylphenyl, tolyl, xylyl, octadecyl phenyl, and the like; naphthyl, indenyl and the like; alkaryl groups; such as benzyl, 6-phenyl-n-hexyl, 14-phenyl-n-tetradecyl, phenyl-n-eicosyl and the like; cycloalkyl groups such as cyclohexyl, methylcyclohexyl, cyclooctyl and the like; alkyl groups such as methyl, n-hexyl, heptacosyl, 2-ethyl-n-hexyl, isopropyl, pentyl, 2,2,4,4,6,6,8,8,-octamethylnonyl, 2,4,6-trimethylheptyl, n-heptadecyl, n-tetradecyl and the like. Preferred organic radical substituents are the hydrocarbon alkyl radicals having from 1 to about 20 carbon atoms, phenyl, and $C_1$–$C_4$ alkyl substituted phenyl radicals. Examples of these preferred organic radicals are methyl, n-butyl, and the like, tolyl, n-butylphenyl, xylyl and the like. More preferred organic radical substituents are the hydrocarbon alkyl radicals having from 1 to about 9 carbon atoms; aryl groups of up to about 9 carbon atoms such as phenyl; aralkyl groups having up to about 9 carbon atoms such as phenylethyl, 1-phenylpropyl, 2-phenylpropyl, phenylisopropyl and the like; alkaryl groups having up to about 9 carbon atoms such as xylyl, ethylphenyl, and the like; and cycloalkyl groups having up to about 9 carbon atoms such as cyclohexyl, methylcyclohexyl, cyclooctyl and the like; such that the total number of carbon atoms in the allylic alcohol does not exceed about 12. Examples of these preferred organic radicals are methyl, ethyl, n-butyl, iso-butyl, n-pentyl, iso-pentyl, n-hexyl, iso-hexyl, n-heptyl, iso-heptyl, octyl, and the like, phenyl, tolyl, propylphenyl, xylyl, and the like. In preferred allylic alcohols R' is hydrogen; while in more preferred allylic alcohols R' and R or $R_1$ are hydrogen. The most preferred allylic alcohol is allyl alcohol.

The reactant carbonyl compounds are selected from ketones, aldehydes, and mixtures thereof. Preferred ketones are alkyl ketones having from 3 to about 11 carbon atoms. Examples of useful ketones are diisobutyl ketone, cyclohexanone, methylethyl ketone, methyl isobutyl ketone, diamyl ketone, cyclohexyl ethyl ketone, undecanone-4, hexanone-2, nonanone-4, and the like. An especially preferred ketone is acetone. Preferred aldehydes are alkyl aldehydes having from 1 to about 10 carbon atoms. Examples of useful aldehydes are formaldehyde, benzaldehyde, acetaldehyde, n-propanal, cyclohexyl aldehyde, n-decanal, 2-methyl-n-butanal, n-heptanal, butyraldehyde, and the like. Mixtures of the aforesaid aldehydes and ketones can also be used. Examples of useful mixtures of aldehydes and ketones are formaldehyde-diisobutyl ketone, acetaldehyde-diisobutyl ketone, formaldehyde-cyclohexanone, formaldehyde-methylethyl ketone, cyclohexyl aldehyde-diamyl ketone, cyclohexyl ethyl ketone-n-propanal, and the like. The proportions of ketone to aldehyde in the mixture of ketone-aldehyde is not critical and may be varied from about 1% by weight of aldehyde to 99% by weight of ketone to from about 99% by weight of aldehyde to 1% by weight of ketone. Generally, about equal amounts of aldehyde and ketone can be used in the aldehyde-ketone mixture. The amount of ketone, aldehyde, or mixtures thereof used in the present process may be varied. The molar ratio of carbonyl compound:allylic alcohol ranges from about 2:1 to about 1:5; preferably the molar ratio is 1:1 to about 1:2.

Carbon monoxide is also required in the present reaction system. The carbon monoxide is ordinarily added as a gas and its concentration is generally designated in terms of pressure. Ordinarily CO pressures of from 15 to 10,000 psi are useful; CO pressures of 500 to 5,000 psi are conveniently used. Generally, an amount of CO which provides at least about 1 mole of CO per mole of allylic alcohol reacted can be used. There is no real upper limit on the amount of CO used and, therefore, said upper limit is determined by secondary considerations such as expense, design of reaction vessel, and the like.

The catalyst used in the present process is a combination of (1) a Group VIII noble metal salt and (2) a salt of germanium or tin. The Group VIII noble metals include Rh, Ru, Os, Ir, Pt and Pd. Inorganic salts are generally preferred. The halides of the Group VIII metals and tin or germanium, wherein the halide has an atomic number of at least 17, are more preferred. Examples of useful salts of tin and germanium are stannous and stannic chlorides, bromides and iodides, germanium di- and tetrachlorides; germanium tetrabromides, germanium tetraiodides, stannous and stannic sulfates; the phosphates, phosphites, borates, sulfates, sulfites, nitrates, nitrites, carbonates and like compounds of tin and germanium. Examples of suitable salts of Group VIII noble metals are binary compounds such as ruthenium tri- and tetrachloride; rhodium trichloride and tetrachloride; palladium dichloride and dibromide; palladium nitrate; osmium di- and trichloride; iridium tetrabromide and tetrachloride, platinic bromide, platinic chloride, platinous iodide, platinous sulfate, the Group VIII noble metal phosphates, phosphites, nitrates, nitrites, sulfates, sulfites, carbonates, borates and the like; and salts derived from hydrohalo acids exemplified by $K_2RhBr_5$, $Na_3RhBr_6 \cdot 12H_2O$, $BaRhBr_5$, $Na_3RhCl_6 \cdot 18H_2O$, $Li_3RhCl_6 \cdot 12H_2O$, $Na_2RuCl_4$, $Na_2RuCl_6$, $K_2RuBr_5 \cdot H_2O$, $MgPdCl_4$, $ZnPdCl_4$, $BePdCl_6 \cdot 8H_2O$, $MgPdCl_6 \cdot 6H_2O$, $K_2PdI_4$, potassium fluopalladite, $Na_2PdF_4$, $K_4PdCl_6$, $Na_2PdCl_4$, $CaPdCl_6$, $Na_2OsF_6$, $Ag_2OsCl_6$, $Na_2OsBr_6 \cdot 4H_2O$, $K_2OsI_6$, $K_2OsI_4$, $Li_2IrCl_6 \cdot 6H_2O$, $K_3IrI_6$, $Hg_3IrCl_6$, $Na_2IrCl_6 \cdot 6H_2O$, $Na_3IrBr_6 \cdot 12H_2O$, $K_2PtCl_6$, $6H_2O$, $K_2PtCl_4$, $K_2PtBr_4$, $Li_2PtCl_6 \cdot 6H_2O$, $Na_2PtBr_6 \cdot 6H_2O$, $Na_2PtI_4$, $Li_2PtCl_4$, $CaPtCl_6$, $MgPtBr_4$, and the like. The salts of platinum and palladium are preferred.

Especially useful catalyst combinations are salts of tin and platinum or palladium; and most preferably salts of tin and salts derived from Group VIII nobel metal hydrohalo acids. Some specifically preferred catalyst combinations are $SnI_4$ and $K_2PdI_4$; $SnBr_2$ and $Na_2PtCl_4$; $SnBr_4$ and $ZnPdBr_4$; $SnCl_2$ and $K_2PtCl_6$; $SnBr_2$ and $K_2PtBr_4$; $PtCl_4$ and $SnI_2$; $PtCl_2$ and $SnCl_2 \cdot 2H_2O$; and $PdCl_2$ and $SnCl_4$. A most preferred combination is $SnCl_2 \cdot 2H_2O$ and alkali metal salts of haloplatinic acid; e.g., $Na_2PtCl_6$, $K_2PtCl_6$, and $LiPtCl_6$.

Special preparation of the catalyst combination does not appear to be required. In general, the suitable metal salts are added directly into the reaction system. The ratio of the tin or germanium salt to the Group VIII noble metal salt can be varied. Amounts of tin or germanium salt sufficient to provide a tin (or germanium):Group VIII metal atomic ratio ranging from 1:1 up to about 10:1 can be used. The total amount of catalyst combination which can be employed in the process may be varied widely; in general a sufficient amount of the catalyst is provided to permit the reaction to proceed at a reasonable rate under the particular conditions, that is, temperature, pressure, etc., set for the process. That is, generally a catalytic amount of the catalyst is provided. By catalytic amount is meant an effective amount of catalyst for permitting the reaction to proceed at a reasonable rate. Generally, an amount of the catalyst combination which provides about 0.0001 to about 0.2 moles of Group VIII noble metal per mole of allylic alcohol can be used. There is no upper limit on the amount of catalyst used and the upper limit is, therefore, determined by such secondary factors as expense, and the like.

The present reaction is ordinarily carried out at pressures above atmospheric; except where the other reaction ingredients, i.e., the carbonyl compound or the allylic alcohol, have any appreciable vapor pressure at the reaction temperature, the pressure of the system is ordinarily that attributed to the carbon monoxide. As pointed out above, the pressure may range from about 15 psi to about 10,000 psi.

Reaction temperatures may be varied; temperatures ranging up to 300°C. can be used. A reaction temperature range of from 70°C. to 300°C. is conveniently used. Generally, the reaction is carried out at a temperature sufficiently high to coreact the allylic alcohol of formula I with the aforedescribed carbonyl compounds in the presence of CO using the aforedescribed catalyst.

The time of the reaction, of course, will be dependent upon other variables in the system such as the nature of the allylic alcohol, the CO pressure, the reaction temperature and the like. Generally, the reaction parameters, that is, the temperature and pressure, are adjusted so that a good yield is obtained in a reasonable time. Reaction times ranging from 30 minutes up to 24 hours or more can be used.

The products obtained in the present process are a mixture of various unsaturated compounds. A predominant product is a mono-unsaturated alcohol. Although the reaction is not fully understood, the following reaction equation conveniently illustrates the nature of the alcohol product obtained.

-continued

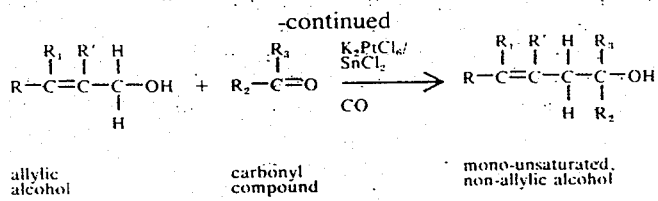

| allylic alcohol | carbonyl compound | | mono-unsaturated, non-allylic alcohol |

R, R' and $R_1$ are as described above; $R_2$ and $R_3$ can be H and/or $C_1$–$C_9$ alkyl groups. As the equation illustrates when formaldehyde is the carbonyl compound ($R_2$ and $R_3$ = H) then a primary alcohol product results; with other aldehydes ($R_2$ or $R_3$ = H) the product alcohol is secondary; while with ketones ($R_2$ and $R_3$ = H) the alcohol produced is tertiary. In addition to the mono-unsaturated alcohol product, traces of polyunsaturated olefins and unsaturated ethers are produced. Reduction of the allylic alcohol also occurs yielding the corresponding monoolefin; for example, allyl alcohol reactant will produce propylene.

The unsaturated alcohol products of this invention have many utilities. They may be used either as mixtures containing the other unsaturated by-products or they can be separated by methods known in the art into their various compounds before use. These unsaturated alcohols may be reduced to prepare the corresponding saturated alcohols; they can be catalytically halogenated to form halogenated alcohols which may be useful as solvents; they can be hydroformylated, that is, reaction with carbon monoxide and hydrogen in the presence of cobalt carbonyl and the product then can be reduced to prepare diols, useful as solvents or polyester intermediates.

The following examples will illustrate the process of the present invention.

EXAMPLE I

Use of $K_2PtCl_6$ as Catalyst Component

An autoclave fitted with a magnetic stirrer was charged with 1450 millimoles (mmoles) of allyl alcohol, 1000 mmoles of acetone, 2.6 grams (g) of $K_2PtCl_6$ and 5.8 g of $SnCl_2 \cdot 2H_2O$. The autoclave was sealed, flushed twice with CO with stirring and finally pressured with CO to about 2000 psi. The mixture was then heated, with stirring, to 90°C., the pressure rising to 3000 psi. The reaction was continued at this temperature for 12 hours. The autoclave was then cooled and vented.

The product obtained was a dark liquid. Conversion of allyl alcohol, based on Gas Liquid Chromatographic (glc) analysis was 100%. The liquid product, on analysis, was shown to contain about 89% $C_6$ mono-unsaturated alkanol ($H_2C=CH-CH_2-C(CH_3)_2-OH$), about 4.5% $C_{12}$ unsaturated ether, about 2% $C_6$ dienes, and about 4.5% allyl ether.

EXAMPLE II

Use of $H_2PtCl_6$ as Catalyst Component

The Example I experiment was repeated using the same reactants in substantially the same quantities; but substituting an equal weight of $H_2PtCl_6 \cdot 6H_2O$ for the $K_2PtCl_6$ catalyst component.

The product obtained was a dark liquid. The conversion of allyl alcohol based on glc analysis was 100%. The liquid product, on analysis, was found to contain about 60% of a mixture of $C_6H_{10}$, $C_{12}H_{22}$, and $C_{18}H_{34}$ dienes and about 30% of $C_6$ monounsaturated alkanol. The remaining 10% of the product is a mixture of other unsaturated compounds.

From a comparison of Example I and Example II processes, the distinction between a Group VIII noble metal salt and a Group VIII noble metal hydrohalo acid as catalyst components is apparent. When a Group VIII metal salt ($K_2PtCl_6$) is used, the product obtained contains a mono-unsaturated alcohol as the primary product with only traces of polyunsaturated olefins (Example I); but when a Group VIII noble metal hydrohalo acid ($H_2PtCl_6$) is used, the polyunsaturated olefin is the major product (Example II).

EXAMPLE III

Using the procedure of Example I, a reaction was run using 974 mmoles of allyl alcohol, 1477 mmoles of acetone, 2.6 g of $K_2PtCl_6$, 5.8 g of $SnCl_2 \cdot 2H_2O$ under an initial CO pressure of 3000 psi (measured at 90°C.) at a reaction temperature of 90°C. and 5 hour reaction time. A liquid product was obtained.

The conversion of allyl alcohol was 66%; and the liquid product contained about 89% $C_6$ mono-unsaturated alkanol, about 4.5% $C_{12}$ unsaturated ether, about 4.5% allyl ether and about 2% mixed $C_6$ dienes.

Similar results are obtained when $K_2PdCl_4$, $PtCl_4$, $Rh_2(SO_4)_3 \cdot 12H_2O$, $IrBr_4$, $CaCsCl_6$, or $RuCl_3$ are used in place of $K_2PtCl_6$; or when $GeCl_4$, $SnCl_4$, $SnBr_2$, $GeI_4$, $SnSO_4$, or $GeBr_2$ are used in place of $SnCl_2 \cdot 2H_2O$ in Examples I or III.

Likewise, substitution of formaldehyde, n-decanal, 2-ethyl hexanal, methyl-ethyl ketone, di-n-pentyl ketone, or mixtures of ketones and/or aldehydes for acetone in Examples I or III produces analogous results.

EXAMPLE IV

Using the procedure of Example I, a reaction was run using 969 mmoles of allyl alcohol, 1448 mmoles of acetone, 2.6 g of $K_2PtCl_6$, 5.8 g $SnCl_2 \cdot 2H_2O$, under an initial pressure of 1000 psi (measured at 90°C.), at a reaction temperature of 90°C. and a reaction time of slightly more than 5 hours. A liquid product was obtained.

The conversion of allyl alcohol was 79%; and the liquid product contained about 81% $C_6$ mono-unsaturated alkanol, about 12% allyl ether, about 5% $C_{12}$ unsaturated ether, and about 2% mixed $C_6$ dienes.

EXAMPLE V

Using the procedure of Example I, a reaction was run using 983 mmoles of allyl alcohol, 1469 mmoles of acetone, 2.6 g of $K_2PtCl_6$, and 5.8 g of $SnCl_2 \cdot 2H_2O$, under an initial CO pressure of 500 psi (measured at 90°C.), at a reaction temperature of 90°C. and a reaction time of 5 hours. A liquid product was obtained.

The conversion of allyl alcohol was 72%; and the liquid product contained about 80% $C_6$ mono-unsaturated alkanol, about 13% allyl ether, about 4% $C_{12}$ unsaturated ether, and about 3% mixed $C_6$ dienes.

Following is a tabulation of a series of examples further illustrating the process of the present invention. In each instance, a primary product obtained is a mono-unsaturated alcohol having a structure analogous to the alcohol product obtained in Example 1.

| | Allylic Alcohol[1] $R-C=CR'-CH_2OH$ having $R_1$ | | Aldehyde/ | | Catalyst | | |
|---|---|---|---|---|---|---|---|
| Ex. | R and R' | $R_1$ | Ketone | (Parts)[2] | | (Moles) | (Moles) |
| 3 | H | $CH_3$ | Butanone-2 | (146) | $Li_2PtCl_4.O$ | (0.0001) | $SnCl_2$ (0.001) |
| 4 | H | $C_{27}H_{55}$ | Cyclohexyl aldehyde | (437) | $Na_2OsF_6$ | (0.1) | $SnCl_2.2H_2O$ (0.8) |
| 5 | H | Phenyl | Diisobutyl ketone | (236) | $PtCl_4$ | (0.05) | $GeCl_2$ (0.35) |
| 6 | H | $C_{12}H_{25}$ | 2-Ethyl-n-hexanal | (363) | $RuCl_3$ | (0.025) | $GeCl_4$ (0.075) |
| 7 | $CH_3$ | $CH_3$ | Formaldehyde | (70) | $MgPdCl_6·6H_2O$ | (0.005) | $SnSO_4$ (0.02) |
| 8 | $C_8H_{17}$ | $C_{19}H_{39}$ | Heptanone-3 | (262) | $Ru(NO_3)_3.6H_2O$ | (0.07) | $SnBr_2$ (0.14) |
| 9 | Benzyl | H | Pinacolone | (224) | $BaRhBr_5$ | (0.2) | $GeI_4$ (0.2) |
| 10 | Naphthyl | $C_3H_7$ | 2-Methyl-n-octanal | (251) | $Hg_3IrCl_6$ | (0.002) | $SnI_2$ (0.018) |
| 11 | Cyclohexyl | $C_{14}H_{29}$ | Isobutylmethyl ketone | (507) | $PdBr_4$ | (0.0003) | $SnBr_4$ (0.007) |
| 12 | Tolyl | Tolyl | 2,2-Dimethyl-n-propanal | (313) | $Pd(NO_3)_2$ | (0.008) | $Ge(NO_3)_2$ (0.04) |
| 13 | Isopropyl | Xylyl | n-Butanal | (156) | $NaRuCl_4$ | (0.0006) | $SnCl_2.2H_2O$ (0.0036) |
| 14 | Dodecylphenyl | $C_2H_5$ | Undecanone-6 | (152) | $IrI_4$ | (0.04) | $SnI_2$ (0.22) |
| 15 | $C_5H_{11}$ | H | n-Decanal | (13) | $PtP_2O_7$ | (0.03) | $GeBr_2$ (0.0225) |
| 16 | t-Butyl | t-Butyl | Cyclohexylmethyl ketone | (68) | $RhCl_3$ | (0.006) | $SnCl_2.2H_2O$ (0.04) |
| 17 | 16-Phenyl-n-hexadecyl | H | Pentanone-2 | (429) | $OsBr_4$ | (0.05) | $Sn(NO_3)_2$ (0.4) |
| 18 | H | H | Methyl ethyl ketone | (65) | $Na_2PtCl_4$ | (0.1) | $SnCl_2.2H_2O$ (0.4) |

| Ex. | CO (Psi) | Temp (°C) | Reac. Time (Hrs) |
|---|---|---|---|
| 3 | 500 | 75 | 0.5 |
| 4 | 10000 | 30 | 24 |
| 5 | 5500 | 105 | 11 |
| 6 | 2000 | 170 | 6 |
| 7 | 7500 | 230 | 8 |
| 8 | 1250 | 300 | 7 |
| 9 | 8300 | 110 | 1 |
| 10 | 3500 | 250 | 3 |
| 11 | 4800 | 200 | 2 |
| 12 | 2300 | 135 | 4 |
| 13 | 6200 | 280 | 18 |
| 14 | 5000 | 160 | 20 |
| 15 | 1000 | 150 | 14 |
| 16 | 800 | 55 | 0.7 |
| 17 | 9100 | 200 | 16 |
| 18 | 15 | 270 | 10 |

[1]One mole of allylic alcohol is used in each example.
[2]By weight

The process of the present invention and its embodiments have been described above. Claims to this invention are as follows.

We claim:

1. A process for preparing mono-olefinically unsaturated alcohols having the formula

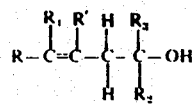

wherein R, R', $R_1$, $R_2$ and $R_3$ have the meanings given below which comprises the reaction of (i) an allylic alcohol having the formula

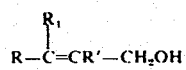

wherein R, R' and $R_1$ are independently selected from the group consisting of hydrogen and alkyl, cycloalkyl, aryl, alkaryl, and aralkyl groups having from 1 to about 9 carbon atoms, and (ii) a carbonyl compound selected from the class consisting of alkyl ketones or alkyl aldehydes and mixtures thereof having the Formula

wherein $R_2$ and $R_3$ are independently selected from the class consisting of hydrogen and alkyl groups having from 1 to 9 carbon atoms, in the presence of an amount of carbon monoxide sufficient to provide at least 1 mole of carbon monoxide for every mole of reacted allylic alcohol, and a catalytic amount of a catalyst combination of (a) an inorganic Group VIII noble metal salt selected from the group consisting of the halides, the sulfates, phosphates, phosphites, carbonates, borates, sulfites, nitrates, nitrites, and salts derived from hydrohalo acids, and (b) an inorganic salt of a metal selected from tin and germanium selected from the group consisting of halides, sulfates, sulfites, phosphates, phosphites, borates, carbonates, nitrates and nitrites, at a temperature and pressure sufficient for said allylic alcohol and said carbonyl compound to coreact in the presence of carbon monoxide and said catalyst to form said unsaturated alcohols.

2. The process of claim 1 wherein said allylic alcohol is allyl alcohol.

3. The process of claim 2 wherein said catalyst is a combination of an alkali metal salt of hydrohaloplatinic acid and tin halide.

4. The process of claim 2 wherein said catalyst is a combination of an alkali metal salt of hydrohalopalladic acid and tin halide.

5. The process of claim 1 wherein said carbonyl compound is a ketone.

6. The process of claim 5 wherein said ketone is acetone.

7. The process of claim 1 wherein said Group VIII metal is platinum.

8. The process of claim 7 wherein said catalyst is a combination of a salt derived from a platinum hydrohalo acid and a tin halide.

9. The process of claim 8 wherein said allylic alcohol is allyl alcohol, said carbonyl compound is acetone, and said catalyst is a combination of $K_2PtCl_6$ and $SnCl_2$.

10. The process of claim 1 wherein said Group VIII metal is palladium.

11. The process of claim 10 wherein said catalyst is a combination of a salt derived from a palladium hydrohalo acid and a tin halide.

12. The process of claim 1 wherein said carbonyl compound is an aldehyde.

13. The process of claim 12 wherein said Group VIII noble metal is platinum.

14. The process of claim 13 wherein said catalyst is a combination of a salt derived from a platinum hydrohalo acid and a tin halide.

15. The process of claim 12 wherein said Group VIII noble metal is palladium.

16. The process of claim 15 wherein said catalyst is a combination of a salt derived from palladium hydrohalo acid and a tin halide.

17. A process for preparing the mono-olefinically unsaturated alcohol 1,1-dimethyl-3-butene-1-ol which comprises the reaction of (i) allyl alcohol, and (ii) acetone, in the presence of an amount of carbon monoxide sufficient to provide at least 1 mole of carbon monoxide for every mole of reacted allyl alcohol, and a catalytic amount of a catalyst combination of (a) $K_2PtCl_6$, and (b) $SnCl_2.2H_2O$, at a temperature and pressure sufficient for said allyl alcohol and said acetone to coreact in the presence of carbon monoxide and said catalyst to form said unsaturated alcohol.

18. A process for preparing the mono-olefinically unsaturated alcohol 1,1-dimethyl-3-butene-1-ol which comprises the reaction of (i) allyl alcohol, and (ii) acetone, in the presence of an amount of carbon monoxide sufficient to provide at least 1 mole of carbon monoxide for every mole of reacted allyl alcohol, and a catalytic amount of a catalyst combination of (a) $K_2PdCl_4$, and (b) $SnCl_2.2H_2O$, at a temperature and pressure sufficient for said allyl alcohol and said acetone to coreact in the presence of carbon monoxide and said catalyst to form said unsaturated alcohol.

* * * * *

UNITED STATES PATENT AND TRADEMARK OFFICE
CERTIFICATE OF CORRECTION

PATENT NO. : 3,956,408
DATED : May 11, 1976
INVENTOR(S) : Raymond A. Schell and Lawrence J. Kehoe It is certified that error appears in the above-identified patent and that said Letters Patent are hereby corrected as shown below:

Column 4, line 3 "nobel" should read -- noble --

Column 8, line 22 "(0.0225)" should read -- (0.225) --

Signed and Sealed this

Fifth Day of October 1976

[SEAL]

Attest:

RUTH C. MASON
Attesting Officer

C. MARSHALL DANN
Commissioner of Patents and Trademarks